United States Patent [19]

Theofilopoulos et al.

[11] 4,342,566

[45] Aug. 3, 1982

[54] SOLID PHASE ANTI-C3 ASSAY FOR DETECTION OF IMMUNE COMPLEXES

[75] Inventors: Argyrios N. Theofilopoulos; Frank J. Dixon, both of La Jolla, Calif.

[73] Assignee: Scripps Clinic & Research Foundation, La Jolla, Calif.

[21] Appl. No.: 123,562

[22] Filed: Feb. 22, 1980

[51] Int. Cl.³ ................... G01N 33/54; G01N 33/56
[52] U.S. Cl. ................... 23/230 B; 422/57; 422/61; 424/1; 424/12; 435/7
[58] Field of Search ............. 435/7; 23/230 B; 424/1, 424/12; 422/57, 61

[56] References Cited

U.S. PATENT DOCUMENTS

| | | | |
|---|---|---|---|
| 4,138,213 | 2/1979 | Masson | 23/230 B |
| 4,141,965 | 2/1979 | Soothill | 23/230 B X |
| 4,153,417 | 5/1979 | Hallgren | 424/1 X |
| 4,162,895 | 7/1979 | Camblaso | 23/230 B X |
| 4,169,138 | 9/1979 | Jonsson | 23/230 B X |
| 4,184,847 | 1/1980 | Hallgren | 424/1 X |
| 4,200,436 | 4/1980 | Mochida | 23/230 B |
| 4,210,622 | 7/1980 | Soothill | 23/230 B X |

OTHER PUBLICATIONS

"Manual of Clinical Immunology," Noel R. Rose et al., eds. Chapt. 91, *American Society for Microbiology*, Washington, D.C., 1976.

*Primary Examiner*—Sidney Marantz
*Attorney, Agent, or Firm*—Knobbe, Martens, Olson, Hubbard & Bear

[57] ABSTRACT

A solid phase assay which specifically detects C-fixing ICs by reacting ICs or aggregated gammaglobulin in normal serum with matrix-bound F(ab')2 anti-C3 and measuring the amount of Ig by radioimmunoassay or enzyme-linking techniques, and means for carrying out the assay are disclosed.

5 Claims, 8 Drawing Figures

SOLID PHASE ANTI-C3 ASSAY FOR DETECTION OF IMMUNE COMPLEXES

This invention relates to immunochemistry and, more specifically, to the detection and measurement of immune complexes (ICs) as an aid in diagnosis and treatment of diseases.

BACKGROUND

Upon exposure to most antigens, an individual responds by synthesizing specific antibodies that subsequently may interact with the inciting antigens and unite noncovalently with them to form immune complexes (ICs). This course of the normal immune response is designed to eliminate and/or neutralize the antigens, thus benefiting the host. However, there is no doubt that formation of ICs under some circumstances is detrimental to the host.

The harmful effects of ICs were first suggested at the beginning of this century by von Pirquet (1911), who proposed that the onset and course of serum sickness were determined by toxic factors produced by the interaction of host antibody and antigen in the circulation. Thereafter, others made similar observations (Longcope, 1915; Rich and Gregory, 1943; Hawn and Janeway, 1947). The definite pathogenic role of the ICs was shown during the 1950's by the work of Germuth (1953), Germuth and McKinnon (1957), Germuth et al (1957), Dixon and associates (1958, 1961), and Dixon (1963), who confirmed and amplified von Pirquet's original theory using the experimental rabbit model of "one shot" serum sickness. It was demonstrated that the onset of glomerulonephritis and generalized vasculitis coincided with the appearance of soluble ICs in rabbits' circulations, a decrease in serum complement (c) activity, and a deposition of ICs in the sites of injury (Dixon, 1963; Dixon et al, 1958, 1961).

In vivo and in vitro experiments have more recently clarified many factors involved in IC formation, removal, and localization as well as the mechanisms of IC-induced inflammatory reactions. Moreover, ICs are now viewed, apart from their potential phlogogenicity, as regulators of both cellular and humoral immune responses by virtue of their capacities to interact with antigen receptor-bearing lymphocytes and subpopulations of T and B cells, as well as with unclassified lymphocytes and macrophages having Fc and C receptors. With the recognition of the immunopathologic consequences of ICs and the development of new techniques for demonstrating ICs in tissues and biological fluids, considerable evidence has accumulated substantiating the primary pathogenic significance of ICs in a variety of animal and human diseases.

Circulating soluble ICs in man and lower animals are responsible for, or associated with, a diverse array of diseases. These include autoimmune disease, neoplastic diseases, infectious diseases due to bacteria, viruses and parasites, and other unclassified disorders.

Both exogenous and endogenous antigens can trigger pathogenic immune responses, resulting in IC disease. The awareness of IC's important role in many diseases has stimulated development of techniques for demonstrating them in tissues and biological fluids.

The presence of ICs in pathologic tissue specimens can be inferred from several lines of evidence. Histologically, the patterns of injury may appear similar to those known to occur in experimental animals in which IC disease has been induced (Wilson and Dixon, 1976). Presumed IC deposits in tissues can be identified also by electron microscopy and by conventional histochemical techniques. Of the immunohistochemical techniques, the most widely used is immunofluorescence (Wilson and Dixon, 1976), which allows Ig, C components, and in some cases specific antigens, to be identified. When these materials deposit in a granular, discrete pattern, in all likelihood the individual has an IC disorder. In addition, if enough of the diseased tissue is available, deposited ICs can be eluted from it by using low pH buffers (citrate buffer, HCl-glycine buffer) (Oldstone, 1975a; Koffler et al, 1971; Woodroffe and Wilson, 1977; Bartolotti, 1977) or chaotropic agents (KI, KSCN) (Edgington, 1971; Woodroffe and Wilson, 1977), etc., after which the antibodies and sometimes the antigens can be recovered, quantitated, and identified (see Section VI).

Recently, interest has increased in developing immunologic techniques for demonstrating ICs directly in bodily fluids.

Although historically the development of assays for soluble ICs started with physiochemical rather than immunologic techniques, the latter are more commonly used now. It is useful to divide all the available methods into two main groups; antigen-specific tests, that is, detection of a specific antigen complexed with antibody or, by far the larger and more readily applicable group, antigen-nonspecific tests.

TABLE I

ANTIGEN-NONSPECIFIC METHODS FOR DETECTING CIRCULATION IMMUNE COMPLEXES

1. Physical techniques
Analytical ultracentrifugation
Sucrose density gradient centrifugation
Gel filtration
Ultrafiltration
Electrophoresis
Polyethylene glycol (PEG) precipitation
Cryoprecipitation
2. Methods based on the biologic characteristics of immune complexes
    a. Complement techniques
    Microcomplement consumption test
    Assays based on the interaction of ICs with purified Clq (Clq precipitation in gels, Clq-PEG test, Clq deviation tests, Clq solid-phase radioimmunoassays)
    Assays of breakdown products of C3 and Cl
    The C3 precipitation assay
    The conglutinin radioimmunoassay
    b. Antiglobulin techniques
    Rheumatoid factor tests
    Other antiglobulin tests
    c. Cellular techniques
    The platelet aggregation test
    Inhibition of antibody-dependent cell-mediated toxicity
    Intracytoplasmic staining of polymorphonuclear leukocytes
    Release of enzymes from eosinophils and mast cells
    The macrophage inhibition assay
    Rosette inhibition tests
    The Raji cell assay
    The L1210 murine leukemia cell assay
    The human erythrocyte assay d. Other methods
Binding to staphylococcal protein A The inventors have summarized studies related to the formation, localization, and fate of ICs and their biologic activities, and described in considerable detail the currently available methods for detecting circulating ICs, the application of these methods to studying IC-associated human diseases, and the state of present attempts to isolate and characterize circulating ICs. (ADVANCES IN IMMUNOLOGY, Vol. 28, pp. 89–220, THE BIOLOGY AND DETECTION OF IMMUNE COMPLEXES[1], Argyrios N. Theofilopoulos and Frank J. Dixon). This summary report is fully incorporated herein by reference. (The works referred to above are specifically identified at pp. 189–220, Vol. 28, ADV. IN IMMUNOLOGY).

DISCLOSURE OF THE INVENTION

ABBREVIATIONS:

DEAE—diethylaminoethylcellulose
AGG—aggregated gamma globulin
BBS—borate buffered saline
BSA—bovine serum albumin
EDTA—ethylene diamino tetraacetic acid
HSA—human serum albumin
IC—immune complexes
NHS—normal human serum
PBS—phosphate buffered saline
RF—rheumatoid factor
SDG—sucrose density gradient
SLE—systemic lupus erythematosus

SUMMARY DISCLOSURE

Although the formation of antibodies against antigens and subsequent formation of immune complexes is meant to protect the host, in some circumstances the continuity of this process, or its intensity, may be harmful to the body. Considerable clinical and laboratory evidence is now available indicating that immune complexes play an important role in several autoimmune, infectious and neoplastic diseases.

Most of the pathogenic effects of immune complexes are believed to be due to their ability in activating the complement system, followed by release of various phlogogenic mediators from mononuclear cells. Being present and related to so many pathologic situations, immune complexes have deserved a great deal of attention and recently numerous techniques have been developed for their detection in biological fluids in the hope that their measurement may help in understanding pathogenesis, prognosis and in monitoring therapy. However, the reagents utilized in these assays may give falsely positive or negative results due to various interfering substances.

A new assay in which complement fixing immune complexes are specifically detected. In this new assay an anti-C3 antibody is fixed to a solid matrix, serum samples and standards are permitted to interact and the amount of immunoglobulin bound to the solid matrix through the C3-anti-C3 reaction is measured by a second reaction with a radio or enzyme-labeled anti-Ig or staphylococcal protein A. The test is easy to perform, the reagents are easily preparable and stable. It is reproducible and can detect 6$\mu$ of aggregated gammaglobulin per ml of serum. The reagents utilized and the procedure are outlined below.

Isolation of F(ab')2 anti-C3: Hyperimmune anti-C3 serum is prepared by repeatedly injecting goats with purified human C3. The IgG fraction of this antiserum is prepared by ammonium sulfate precipitation and DEAE chromatography. F(ab')2 fragments are prepared and used instead of the whole IgG molecule to avoid interference by endogenous rheumatoid factors in the test samples. This is done by pepsin digestion in 0.1 M acetate buffer, pH 4.1, for 18 hours at 37° C., with an enzyme: substrate ratio of 2:100. The reaction is stopped by neutralization with 1.0 M Tris and the F(ab')2 fragments are isolated by gel filtration through Sephadex G-150. Elution is carried out with borate buffered saline (0.2 M borate, 0.075 M NaCl, pH 7.5-BBS). The F(ab')2 peak is collected, pooled and concentrated if necessary. Sodium azide is added as preservative or it can be stored frozen. The best concentration to be used in the assay (see below) is determined by running standard curves with different concentrations of F(ab')2. We have been using concentrations of 1-2 mg/ml but this is expected to vary depending on the amount and avidity of the antibody.

Radioiodinated or enzyme-linked IgG anti-human IgG:

Goat anti-human IgG serum is used. The IgG fraction is prepared as described for the anti-C3 anti-serum, but the whole IgG molecule is used instead of the F(ab')2 fragments. It is radiolabeled with $^{125}$I by the Chloramine T method to give a specific activity of 0.3–0.5 $\mu$Ci/$\mu$g and diluted in 1% human serum albumin in BBS (HSA-BBS), to a final concentration of 100 $\mu$g/ml. Alternatively, we have utilized enzyme-linked instead of radiolabeled antibody anti-human IgG. The anti-human IgG is linked to horseradish peroxidase (HRPO) at a ratio of 8 mg of IgG per 4 mg of enzyme following the procedure described by Wilson and Nakane (53).*

*See references at the end, all of which are incorporated fully herein.

Standards and samples: Aggregated human gamma-globulin (AHG) is prepared by heating human Cohn Fraction II dissolved in phosphate buffered saline (0.01 M at 3000 rpm for 15 min., in order to remove large aggregates, this preparation is stored in 1% HSA-BBS at a concentration of 1 mg/ml, at −70° C., remaining active for several months. For the standard curve, serial dilutions of AHG in HSA-BBS, containing 20 $\mu$g to 78 ng are added to 25 $\mu$l of normal human serum, freshly collected or stored at −70° C. (as source of complement) and incubated at 37° C. for 15 min. After this period, HSA-BBS containing 0.01 M EDTA (HSA-BBS-EDTA) is added, to give a final dilution of 1/21, and 100 $\mu$l are transferred to wells of flexible microtiter plates for reaction with the anti-C3 antibody. The standard curve so prepared corresponds to concentrations of 800 to 3.0 $\mu$g AHG/ml of serum. The serum samples are prepared by simple dilution (1/21) in the same diluent buffer and 100 $\mu$l are added per well. Blood is collected in tubes containing EDTA (final concentration of 0.01 M) and plasma is collected by centrifugation. Serum can be used but should not be frozen and thawed many times so as to avoid complement activation.

Assay method: Flexible microtiter plates (Dynatech Laboratories Inc., Alexandria, VA) are coated with F(ab')2, 100 $\mu$l per well, dissolved in BBS, pH 7.5. Plates are left overnight at 4° C., or 2-3 hours at 37° C. with the same binding efficiency. F(ab')2 is then aspirated (it can be reused at least 2 times for coating new plates), 200 $\mu$l of 1% HSA in BBS, pH 7.5 are added per well, to cover unreacted sites, and the plates are let standing at room temperature for 1 hour. In the meantime, standards and samples are prepared. The HSA-BBS is aspirated off, the plate is washed once with BBS, samples and standards are added (100 μl per well), and the plate is incubated at 37° C. for 2 hours. After 5 washes with BBS, 10 μg of $^{125}I$ goat anti-human IgG is added, dissolved in 1% HSA-BBS, 100 μl per well. The plate is again incubated at 37° C. for 2 hours. After this final incubation, the radioactive antibody is aspirated off, the plate is washed 5 times with BBS and dried up. Finally the wells are cut and counted in a gammacounter.

When utilizing enzyme linked antibody, after the final washes 200 μl of ABTS [2,2'-azino-di (3-ethyl-benzthiazoline sulphonic acid-6) ammonium salt] 1 mg/ml of 0.1 M citrate-phosphate buffer, pH 4.0 and 0.003% $H_2O_2$, are added per well. After color development for 10–15 min. at room temperature, the reaction is stopped by addition of 50 μl of 37 mM NaCN. The content of each well is diluted to 1.0 ml and the OD read at 415 nm.

Clinical application: We have applied the assay to various human sera and good concordance was obtained with the Raji cell (2) and conglutinin (3) assays previously described, as far as positive and negative results. High levels for circulating immune complexes were found in systemic lupus erythematosus, rheumatoid arthritis, Sjögren's and Reiter's syndromes, subacute bacterial endocarditis and acute glomerulonephritis.

TABLE II

ANTI-HUMAN C3 ASSAY APPLIED TO SEVERAL HUMAN PATHOLOGIC CONDITIONS FOR THE DETECTION OF CIRCULATING IMMUNE COMPLEXES

| | N | μg AHG/ml (means ± SEM) | % Positivity* |
|---|---|---|---|
| Normal Controls | 42 | 9.9 ± 2.53 | |
| Rheumatoid Arthritis | 22 | 234.7 ± 57.88 | 68.0 |
| Systemic Lupus Erythematosus | 20 | 270.8 ± 117.73 | 37.0* |
| Sjören's Syndrome | 22 | 356.3 ± 113.64 | 82.0 |
| Reiter's Syndrome | 25 | 406.2 ± 93.95 | 52.0 |
| Subacute Bacterial Endocarditis | 20 | 183.1 ± 38.22 | 45.0 |
| Acute Glomerulonephritis | 20 | 432.8 ± 164.38 | 30.0 |

*Values considered positive above 43 μg AHG/ml (mean ± SD for normal population = 9.9 ± 16.41)
**Includes patients with active and inactive SLE Moreover, we have applied the assay to the analysis of sera from mice with autoimmune diseases and rabbits with chronic serum sickness by utilizing species specific reagents, and shown the applicability of the assay to animal models of diseases. Thus, the anti-C3 assay has several advantages over other assays: (1) it is specific and detects all complement-fixing immune complexes, independently of their ability to activate the classical or alternative pathways; (2) the reagents are stable and easy to prepare; (3) by using as a final reagent antisera against various isotypes and against suspected antigens, both the nature of the antibody and antigen involved in the immune complexes can be determined; (4) by using appropriate antisera to C3 and IgG it can be applied to different animal species; (5) as a solid phase immunoassay the principle of enzyme linked immunoassays (ELISA) can be easily applied, so precluding the use of radioisotopes in the assay.

BEST MODE FOR CARRYING OUT THE INVENTION

INTRODUCTION

Immune complexes (ICs)[1] unquestionably play a pathogenic role in many infectious, autoimmune and neoplastic diseases (reviewed in 1); therefore numerous antigen-specific and antigen-nonspecific assays have been developed to detect such complexes (reviewed in 1). Antigen-nonspecific techniques have the wider applicability because in so many immunologic diseases the etiologic agents are unknown. These antigen-nonspecific methods measure certain physicochemical characteristics of antigen-antibody complexes as well as their interactions with cellular Fc and C3 receptors and with certain serum components such as rheumatoid factors (RF), complement (c) and conglutinin. Although the use of these techniques in human and animal diseases has provided much useful information in regard to immunopathology, prognosis and follow-up of immunologic disorders, several drawbacks limit their usefulness. First, some of the purification procedures are technically difficult or overly time-consuming. Second, and more importantly, many of these assays detect interfering non-IC substances which may lead to false positive or negative results. We present here a simple, sensitive and reproducible solid phase radioimmunoassay for the detection of C-fixing ICs. Our strategy was to interact matrix-fixed F(ab')2 anti-C3 with C-fixing ICs after which the bound IG was detected with radiolabeled anti-Ig antibodies. By using this procedure C-fixing ICs were detected in humans with a variety of diseases, mice with genetic autoimmune disorders and rabbits with serum sickness. When the IC-positive human sera were tested further to characterize the anti-C3 binding ICs, some sera had heavy (>19S) and intermediate 8-19S) size complexes; other samples contained predominantly light (7-8S) anti-C3 reactive materials that seemed to be IgG associated with small C3 fragments.

MATERIALS AND METHODS

Monomeric and Aggregated Gamma Globulins: Monomeric IgG was purified from human, mouse and rabbit Cohn Fraction II (Miles Laboratories, Inc., Elkhart, Ill.; Hyland Laboratories, Costa Mesa, Calif.) by DEAE chromatography and rendered free of aggregates by ultracentrifugation at 150,000 g for 90 min. Aggregated gamma globulins (AGG) were prepared from the respective Cohn Fraction II by heating a solution in phosphate buffered saline (PBS) at 63° C. for 30 min. After centrifugation at 3,000 rpm for 15 min. to remove large insoluble aggregates, the preparations were stored in small aliquots at −70° C. and used throughout the study.

Antisera: Hyperimmune goat anti-human C3 serum was a generous gift from Dr. H. J. Müller-Eberhard (Scripps Clinic and Research Foundation). This antiserum was monospecific as shown by double immunodiffusion against human serum and isolated human C3. The antiserum reacted with native human C3 as well as its fragments C3b, C3c and C3d and was devoid of any activity against human immunoglobulins. All other antisera used in these studies were produced in goats and purchased from Cappel Laboratories (Cochranville, Pa.). Goat anti-mouse C3 and goat anti-rabbit C3 each formed a single line with the respective sera during double immunodiffusion. F(ab')2 fragments of anti-human, anti-mouse and anti-rabbit C3 were prepared by a modification of the method of Nisonoff et al. (2). Briefly, IgG fractions of these antisera were submitted to pepsin digestion in 0.1 M acetate buffer, pH 4.1, with an enzyme to substrate ratio of 2:100 (w/w) for 18 hours at 37° C. After neutralization with 1.0 M Tris, F(ab')2 was separated from the other fragments by gel filtration on Sephadex G-150 with borate buffered saline (BBS) as the eluting buffer. The preparations were free of intact IgG and Fc fragments as shown by polyacrylamide gel electrophoresis and by double immunodiffusion.

Radioiodination: IgG fractions of goat anti-human, anti-mouse or anti-rabbit IgG, F(ab)2 anti-human C3, human IgG, bovine serum albumin (BSA) and anti-BSA were labeled with $^{125}I$ or $^{131}I$ as described by McConahey and Dixon (3) to a specific activity of 0.3–0.5 $\mu Ci/\mu g$ of protein. Radiolabeled goat IgG anti-human and anti-mouse IgG were diluted in 1% human serum albumin (HSA)-BBS or 1% BSA-BBS, pH 7.5, respectively, and radiolabeled anti-rabbit IgG was diluted in BBS without carrier protein. All the radiolabeled proteins were stored at 100 $\mu g/ml$.

Test Sera: Sera from healthy individuals (n=42) and from patients with SLE (n=24), rheumatoid arthritis (n=22), Sjögren's (n=22) and Reiter's (n=25) syndromes, infectious endocarditis (n=20), acute glomerulonephritis (n=20) and malignancies (n=51) were analyzed. Aliquots of these sera were stored at −70° C. and thawed once. Plasmas from some of these patients were obtained by collecting the blood in 0.01 M EDTA (Ethylenediamine tetra-acetic acid; final concentration). Serum samples of immunologically normal mice (C3H/St, BALB/c) and SLE-prone mice (MRL/1, BXSB, NZBxW) were also tested. The number, age and sex of the mice examined are given in the Results section. The immunopathologic characteristics of the SLE-prone mice have been detailed (4). Sera from 6 normal rabbits and 5 rabbits with chronic serum sickness resulting from injections of BSA were kindly provided by Drs. C. B. Wilson and T. J. Neale (Scripps Clinic and Research Foundation). The sera from the rabbits with serum sickness were drawn before and 10, 30 and 60 min. after the daily injection of BSA (5).

Quantitation of IgG and C3: IgG in serum samples and gradient fractions and C3 in the normal human serum used as C source were quantitated by radial immunodiffusion (6).

Detection of ICs: The solid phase anti-C3 radioimmunoassay for circulating ICs were performed was follows: Wells of U-shaped flexible microtiter plates (Dynatech Laboratories, Inc., Alexandria, Va., Catal. No. 1-220-24) were coated with 100 $\mu l$ of F(ab')2 anti-C3 in BBS (1 mg/ml), pH 7.5, and incubated at 4° C. overnight. The material was then aspirated and 200 $\mu l$ of 1% HSA-BSS, pH 7.5, was added to each well to cover unreacted sites. After standing for 1 hr. at room temperature, the wells were washed once with BBS, pH 7.5. To these wells we added 100 $\mu l$ of serum samples diluted 1/21 in 1% HSA-BBS-0.01 M EDTA and standards containing various amounts of AGG (3 to 800 $\mu g$ AGG/ml) in normal human serum (C source). The various amounts of AGG in fresh serum were incubated for 15 min. at 37° C. before being diluted to 1:21 with the diluent buffer. For murine sera, BSA was used instead of HSA in the diluent buffer whereas for rabbit sera the carrier protein was omitted. After incubation for 2 hours at 37° C., the wells were washed 5 times with BBS, and 100 $\mu l$ (10 $\mu g$) of radioiodinated goat IgG fraction of anti-IgG (human, mouse or rabbit) were added. After further incubation (2 hrs., 37° C.), the plates were again washed 5 times with BBS and dried, and then each well was cut free and counted. The uptake in each well was referred to the standard curve and results were expressed as $\mu g$ AGG equivalent per milliliter of serum. For comparison levels of IC-like materials in test sera were also determined by the Raji (7) and the conglutinin (8) assays as described.

Titration and Absorption of RF: Titers of IgM RF in serum samples were determined by the latex agglutination test (9). To determine whether IgM RF could cause false positive results in the assay and whether C-fixing ICs detected in sera or patients with rheumatoid arthritis or Sjögren's syndrome and in sera of MRL/1 mice contained IgM RF, selected sera were absorbed on IgG-Sepharose. 10 $\mu l$ of serum were incubated with 200 $\mu l$ of human or mouse IgG-Sepharose containing 3 mg of the respective IgG per milliliter of packed gel. As a control, portions of the same sera were absorbed on BSA-Sepharose. After incubation for 18 hrs. at 4° C., the Sepharose was removed by centrifugation, and the supernatants were tested for ICs with the anti-C3 assay and for IgM RF activity by latex agglutination.

Sucrose Density Gradient (SDG) Fractionation: To determine the size of the materials that were detected in the anti-C3 assay we sampled sera from 6 healthy donors and 12 IC-positive patients (one with SLE and proliferative glomerulonephritis; two with SLE but no clear renal involvement, two with Reiter's syndrome, two with Sjögren's syndrome, one with acute glomerulonephritis, one with seropositive and one with seronegative rheumatoid arthritis, one with Felty's syndrome and one with chronic granulocytic leukemia in blastic crisis). Sera were diluted 1:2 in PBS, and 300 μl portions were placed on the top of 4.5 ml tubes containing 10–40% sucrose gradients in PBS. Sera were centrifuged at 190,000 g for 15 hrs. using a SW60.1 Beckman rotor. Fifteen fractions were collected from the bottom of the tube and analyzed for levels of IgG by radial immunodiffusion and for positivity in the anti-C3 and conglutinin radioimmunoassays. Because the IgG content of fractions from the different sera varied after SDG centrifugation, binding activity in the anti-C3 assay was expressed as ng of radiolabeled anti-human IgG bound per mg of IgG×ml$^{-1}$ in a given fraction. To verify that IgG bound to anti-C3 during the solid phase assay was indeed associated with C3 fragments, precipitation and inhibition experiments were performed. For precipitation, test fractions were treated with anti-C3 in antibody excess (2 hrs., 37° C.), and supernatants obtained after centrifugation (3,000 rpm, 20 min.) were retested in the solid phase anti-C3 assay; binding activity was compared to that of unmanipulated fractions. For inhibition, test fractions were incubated (30 min. at 37° C. and overnight at 4° C.) with isolated conglutinin (2.5 μg/ml final concentration), and the inhibition of binding was assessed by the solid phase anti-C3 method.

Solubilization of ICs: To evaluate whether C can solubilize IC and free antibody from antigen, we reacted affinity purified, $^{131}$I-rabbit IgG anti-BSA with $^{125}$I-BSA at equivalence for 30 min. at 37° C. and overnight at 4° C. Precipitates containing 15 μg of $^{131}$I-IgG anti-BSA and 2.2 μg of $^{125}$I BSA were mixed with 0.5 ml fresh normal human serum as the solubilizing agent at 37° C. for 1 hr. (10). The serum was then subjected to SDG analysis as described above. Fractions corresponding to the 7S peak were pooled and reacted with goat anti-human C3serum, anti-human transferrin or anti-BSA all in antibody excess, or with normal goat serum. Precipitates obtained after centrifugation were washed twice in cold PBS and counted for radioactivity. Percentages and moles of antigen and antibody present in each fraction of the SDG ultracentrifuged serum and in immunoprecipitates of the fractions around the 7S position were calculated. Corrections for $^{131}$I isotype decay were carried out when indicated.

RESULTS

SOLID PHASE ANTI-C3 RADIOIMMUNOASSAY:

Binding of F(ab')2 Anti-C3 to Microtiter Plates: The amount of F(ab')2 anti-human C3 bound to microtiter plates were measured at different concentrations (0.25 to 8 mg/ml), acidites (pH 6.5 to 9.5), intervals (2 to 18 hours) and temperatures (4-20-37° C.) of incubation. At neutral pH and after overnight incubation at 4° C., the amount of bound anti-C3 increased with increasing concentrations as expected. The binding was better at pH 7.5 than at lower or higher acidities, and approximately the same after incubation at 37° C. for 2 hours, room temperature for 5 hours or 4° C. for 16 hours. The concentration of 1.0 mg/ml was chosen since higher concentrations did not improve the assay's sensitivity nor the slope of the standard curve with serum containing AGG. For practical reasons incubation lasted overnight at 4' C. to coat the plates with anti-C3.

Figure 1:
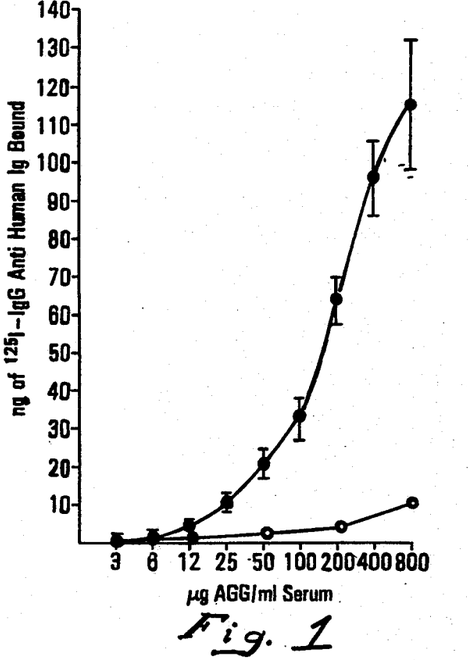
FIG. 1 is a graph depicting binding of AGG in the presence of fresh NHS and EDTA-NHS to anti-C3.

Binding of AGG to Anti-C3 Coated Plates: As shown in FIG. 1, the binding of AGG to the anti-C3 coated wells depended on activation of C and binding was proportional to the amount of AGG added to normal serum. A sensitivity of 6 μg AGG/ml serum was consistently obtained. Data not shown indicated that, at a concentration of 400 μg $^{125}$I labeled AGG/ml serum, approximately 110 μg precipitated with anti-C3 serum in antibody excess and that at concentrations about 800 μg of AGG/ml of serum the amount of AGG precipitated by anti-C3 remained constant (~200 μg). These results were obtained with the normal human serum used throughout the study as the source of C for the standard curve and containing 1.45 mg/ml of C3. Apparently, no additional C was available for binding above 800 μg AGG/ml serum, which we therefore adopted as the upper point of the standard curve.

Plates coated with F(ab')2 anti-human C3 and stored at 4° C. consistently produced standard curves of binding activity for at least three months, although for the present study plates were prepared just the day before the assay. The same F(ab')2 anti-C3 could be used at least three times for coating new plates with no apparent loss of activity.

Reproducibility of the Assay and Effect of Freezing and Thawing, EDTA, Monomeric Ig and other Substances: No significant effect on IC levels was observed after 5 cycles of freezing (−70° C.) and thawing (22° C.) of three serum samples containing 200 μg AGG/ml. Similarly, freezing and thawing of sera from five normal volunteers did not convert the test results from negative to positive. When multiple samples (6–10) of 3 positive sera were tested within the same day, the variability of results did not exceed 5%. When 5 IC-positive human sera were tested consecutively for 3 days, using the same anti-C3 coated plates and radiolabeled anti-IgG antibody, the variability was 9.5%. Adding EDTA to a serum containing AGG and previously interacted with C not only did not prevent the binding of AGG to the anti-C3 but actually increased the binding of AGG+C 10% above that in EDTA-free samples. High levels of monomeric IgG seemed to interfere with the results, but the difference in binding between monomeric IgG and AGG in serum was more than 2 log units. Thus, 10 mg of isolated human monomeric IgG added together with 0.01 M EDTA to a sample of normal human serum containing 12.5 mg/ml of endogenous IgG yielded uptake values in the anti-C3 assay that resembled uptake by the same normal serum to which 50 μg AGG was added.

Removal of IgM RF activity from 5 IC-positive sera from rheumatoid patients and 5 IC-positive sera of MRL/1 mice by using Sepharose-IgG had no effect on activity in the anti-C3 assay. Nor did heparin (200 μg/ml), lipopolysaccharide (LPS, 2 μg/ml) or DNA (2-50 μg/ml) convert normal human sera to positive.

DETECTION OF ICs IN SERUM:

Forty-two human serum samples obtained from healthy volunteers were analyzed with the anti-C3 assay and the mean value ±SEM was 9.9±2.5 μg AGG eq/ml. In comparison, high levels (above 2 SD of normals) and incidences of ICs were found in sera of patients with SLE, rheumatoid arthritis, Sjögren's and Reiter's syndromes, infectious endocarditis and acute glomerulonephritis.

TABLE III

INCIDENCE AND LEVELS OF ICs IN PATHOLOGIC SERA TESTED BY THE ANTI-C3 ASSAY

|  | CASES | μg AGG/ml (mean ± SEM) | % POSITIVE* |
|---|---|---|---|
| Systemic Lupus Erythematosus | 24 | 168.2 ± 35.0 | 75 |
| Rheumatoid Arthritis | 22 | 234.7 ± 57.8 | 73 |
| Sjögren's Syndrome | 22 | 356.3 ± 113.6 | 82 |
| Reiter's Syndrome | 25 | 406.2 ± 93.9 | 56 |
| Infectious Endocarditis | 20 | 183.1 ± 38.3 | 45 |
| Acute glomerulonephritis | 20 | 432.8 ± 164.3 | 30 |
| Malignancies: |  |  |  |
| Breast Cancer | 38 | 69.2 ± 11.8 | 21 |
| Lung Cancer | 13 | 66.2 ± 16.6 | 31 |
| Normal Controls | 42 | 9.9 ± 2.5 |  |

*Sera with activity higher than 2SD above the mean of normal controls (9.9 ± 16.4) were considered positive. The mean values of ICs were derived from sera recorded as positive.

The incidence of positivity in the anti-C3 assay generally lay intermediately between that in the other two assays (Raji and conglutinin assays), with the Raji cell assay giving more positive results.

TABLE IV

INCIDENCE AND CONCORDANCE OF RESULTS BY RAJI, ANTI-C3 AND CONGLUTININ RADIOIMMUNOASSAYS IN HUMAN SERA TESTED BY ALL THREE ASSAYS

| DISEASE | NO. CASES | NO. POSITIVE | | | NO. OF SERA WHERE THERE WAS CONCORDANCE BETWEEN TWO TESTS | |
|---|---|---|---|---|---|---|
|  |  | ANTI-C3 | RAJI | CONGLUTININ | ANTI-C3 & RAJI | ANTI-C3 CONGLUTININ |
| Systemic Lupus Erythematosus | 19 | 11 (58)* | 16 (84) | 6 (32) | 12 (63)* | 6 (32) |
| Rheumatoid Arthritis | 18 | 12 (67) | 16 (89) | 7 (39) | 15 (83) | 8 (44) |
| Infectious Endocarditis | 20 | 9 (45) | 12 (60) | 6 (30) | 11 (55) | 15 (75) |
| Reiter's Syndrome | 25 | 14 (56) | 19 (76) | 14 (56) | 16 (64) | 18 (72) |
| Sjögren's Syndrome | 22 | 18 (82) | 18 (82) | 9 (41) | 19 (86) | 10 (45) |
| Total | 104 | 64 (62) | 81 (78) | 42 (40) | 73 (70) | 57 (54) |

*Numbers in parenthesis represent percentages.

Figure 2:
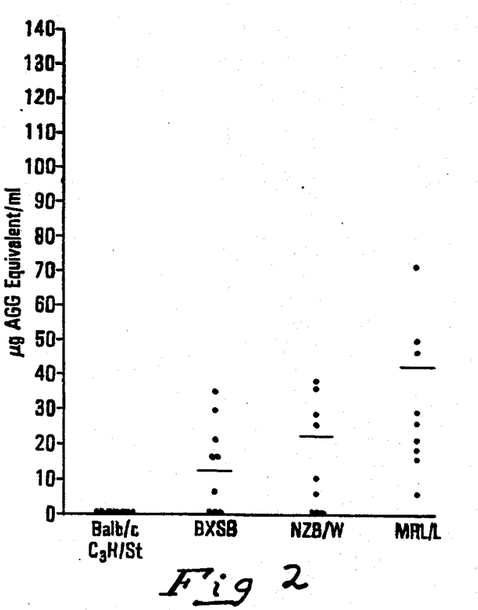
FIG. 2 is a graph depicting levels of ICs in sera of normal and SLE-prone mice by the anti-C3 assay. BALB/c, C3H/St and MRL/1 mice were females or males, NZBxW females and BXSB males. All mice were 5–6 months of age, except the NZBxW which were 8 months old.

In general, sera positive in the anti-C3 assay were also positive in the Raji cell assay. Seventy percent of all sera tested by both assays gave concordant positive or negative results. No correlation was found between titers of RF and levels of IC-like materials as detected by the anti-C3 assay, with samples from seropositive patients having values and incidences (42–500 μg/ml; 75% positive) as high as of those from seronegative patients (44–470 μg AHG/ml; 67% positive). In all three murine strains (NZBxW, BXSB, MRL/1) known to develop spontaneous autoimmune syndromes, in contrast to normal strains, IC-like materials were apparent with the anti-C3 assay (FIG. 2), and MRL/1 mice had the highest values. Sera of rabbits with chronic serum sickness also contained high levels (>800 μg AGG/ml) of circulating IC-like materials that bound to anti-rabbit C3. Unexpectantly, no clear differences were observed in incidences and levels of IC binding among serum samples collected before and after the daily injection of the antigen BSA (data not shown).

Figure 3:
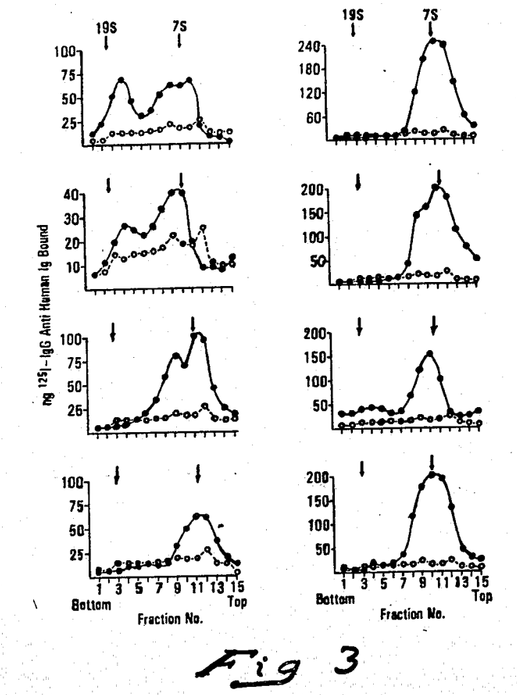
FIG. 3 is a graph depicting anti-C3 binding activity in fractions obtained after SDG centrifugation of pathologic (solid lines) and normal human sera (dotted lines). The position of 19S and 7S markers is indicated by the arrows. (a) Felty's syndrome; (b) SLE with proliferative nephritis; (c) Sjögren's syndrome; (d) acute glomerulonephritis; (e) rheumatoid arthritis; (f) SLE without renal disease; (g) ReiterR's syndrome; (h) chronic granulocytic leukemia in blastic crisis. Three other sera analyzed (SLE without renal disease, Reiter's syndrome, rheumatoid arthritis) showed anti-C3 activity exclusively in the 7-8S fractions whereas another serum (Sjögren's syndrome) showed activity in intermediate (8-19S) fractions.
Figure 4:
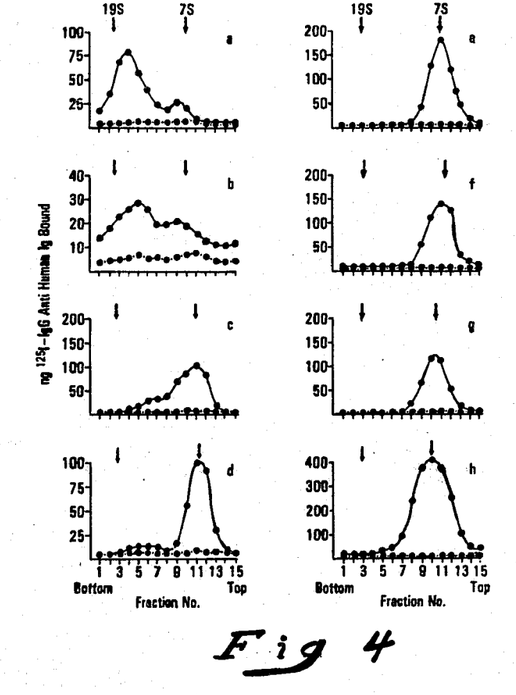
FIG. 4 is a graph depicting conglutinin binding activity in fractions obtained after SDG centrifugation of pathologic (solid lines) and normal human sera (dotted lines). The position of 19S and 7S markers is indicated by the arrows. Same sera as in FIG. 3.

CHARACTERIZATION OF IC-LIKE MATERIALS IN HUMAN SERA DETECTED BY THE ANTI-C3 ASSAY:

Twelve human serum samples showing strong positivity in the anti-C3 assay were subjected to SDG ultracentrifugation. The fractions obtained were individually analyzed for activity in the anti-C3 and conglutinin assays and for IgG levels by radial immunodiffusion. The results obtained with these sera are depicted in FIGS. 3 and 4. As one sees, basically two types of patterns emerged. Some of the pathologic sera exhibited reactivity with anti-C3 and conglutinin in fractions heavier than the 7 S marker whereas others exhibited predominant reactivity in fractions around the 7-8S position.

Figure 5:
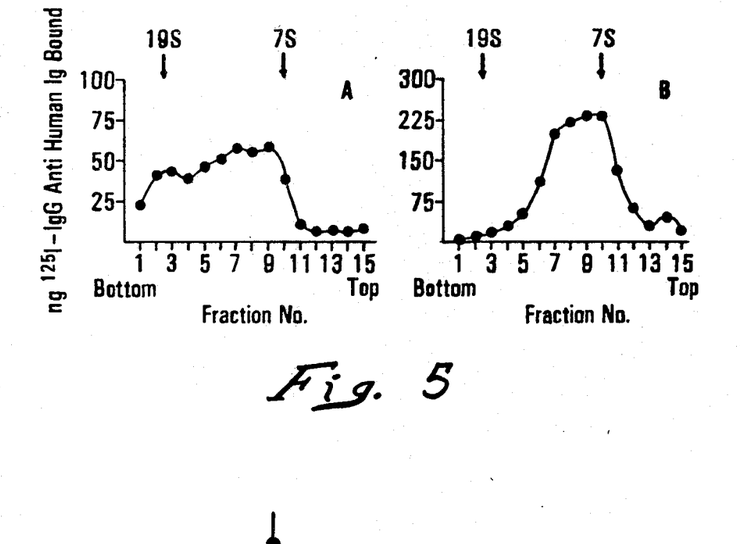
FIG. 5 is a graph depicting anti-C3 binding activity in fractions obtained after SDG centrifugation of a Felty's syndrome serum under neutral (pH 7.4, panel A) and acidic (pH 2.8, panel B) conditions. Note that under acidic conditions (panel B) there is a shift of the anti-C3 activity to the lighter fractions of the gradient.

When a serum from a patient with Felty's syndrome containing heavy anti-C3 reacting materials was ultracentrifuged again in similar gradients made in acidic buffer (Glycine-HCl 0.1 M, pH 2.8), the reactivity with anti-3 shifted to the upper fractions of the gradient (FIG. 5). Although only a small number of samples was analyzed, it is notable that sera of patients with more generalized diseases like lupus proliferative nephritis, Felty's syndrome, Sjögren's syndrome and acute poststreptococcal glomerulonephritis (FIGS. 3 and 4, patterns a,b,c and d) contained heavy reactive IgG, i.e., 8 to 19S and occasionally beyond 19S. In contrast, related to more localized chronic inflammatory conditions like SLE without renal involvement, rheumatoid arthritis without extraarticular manifestations and Reiter's syndrome, the peak of reactivity consistently occupied the 7-8S position (FIGS. 3 and 4, patterns e,f,g,h). Since material from the 7–8S region that reacted with anti-C3 and conglutinin could represent interference by monomeric IgG, all values for binding were compared to the respective IgG concentrations. Even when calculated as binding per mg of IgG X ml$^{-1}$, binding was still much higher in the fraction derived from these pathologic sera (46–90 ng $^{125}$I anti-IgG per mg IgG X ml$^{-1}$) than in those derived from the sera of 6 normal humans (3.4±0.54 ng $^{125}$I anti-IgG per mg IgG X ml$^{-1}$).

To confirm that complexes of IgG and C3 were responsible for reactivity at the 7–8S position, we then pooled corresponding fractions separately from each of three sera that exhibited such activity and treated the pools with goat F(ab')2 anti-human C3, conglutinin or simply buffer (HSA-BBS). After centrifugation (3,000 rpm, 20 min.) to remove immunoprecipitates, the pools were resubmitted to analysis by the anti-C3 assay. As shown in Table V, anti-Ig binding decreased significantly in all three samples after incubation with anti-C3 or conglutinin as compared to controls treated with HSA-BBS.

TABLE V
ANTI-C3 BINDING ACTIVITY IN 7S FRACTIONS OF CERTAIN SERA FOLLOWING TREATMENT WITH BUFFER, FLUID PHASE ANTI-C3 OR CONGLUTININ

| | TREATED WITH | | |
|---|---|---|---|
| | BUFFER | ANTI-C3 | CONGLUTININ |
| Systemic Lupus Erythematosus | 108* | 0(100%)** | 14(87%) |
| Rheumatoid Arthritis | 83 | 0(100%) | 13(84%) |
| Sjögren's Syndrome | 33 | 14(58%) | 12(64%) |

*Values represent ng of $^{125}$I-IgG anti-human Ig bound to F(ab')2 anti-C3 coated plate.
**Numbers in parenthesis express % reduction in comparison with control (buffer values).

Immunoconglutinins are classically described as autoantibodies directed against C3 and its fragments (11). Therefore, we investigated whether the anti-C3 reacting light material found in some sera represented IgG immunoconglutinin or immunoconglutinin-C3 fragment complex. For this purpose, 7-8S fractions from three such sera were incubated (30 min., 4° C.) with C3-Sepharose or BSA-Sepharose (control) and checked again in the anti-C3 assay. No removal of the anti-C3 activity in these light fractions was observed after such treatments, strongly suggesting that the reactivity was not due to IgG immunoconglutinin.

Finally, fractions corresponding to 8-19S and 7-8S position yeilded by SDG centrifugation of 4 positive sera were mixed with 2.5% polyethylene glycol (12). In the resulting supernatants more than 95% of the heavy fractions' binding activity was gone but, as expected, the 7-8S fractions lost less than 5% of this activity.

IN VITRO SOLUBILIZATION OF ICs

Figure 6:
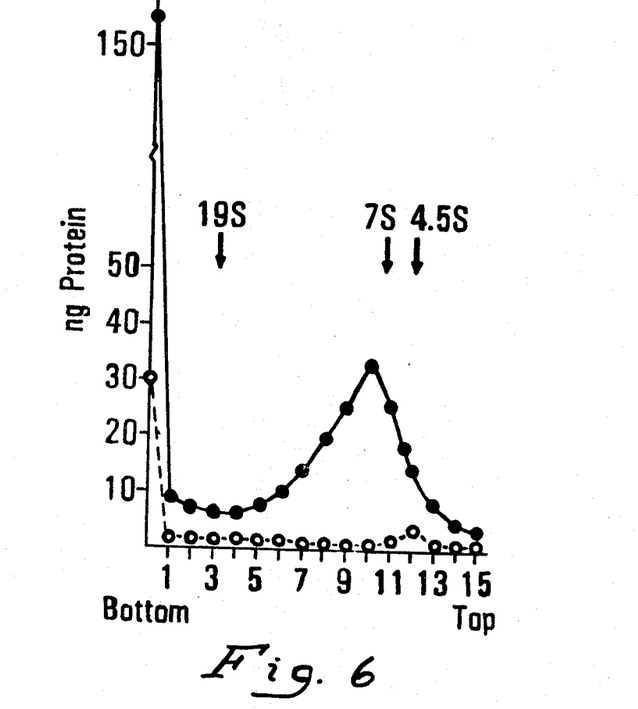
FIG. 6 is a graph depicting SDG analysis of $^{125}I$-BSA-$^{131}I$-anti-BSA complexes made at equivalence and subsequently solubilized with fresh NHS (C source). Note that a substantial amount of the solubilized antibody (31%) migrates in the 7-8S position.

As indicated above, the 7-8S materials detected in some samples of pathologic sera by the anti-C3 and conglutinin assays were apparently composed of IgG associated with C3 fragments. Since solubilization of antigen bound antibody molecules by the C system (10) could produce such complexes, we directly examined their generation after solubilizing BSA-anti-BSA complexes with human C. Radiolabeled antigen-antibody complexes were formed at equivalence, and incubated with fresh human serum at 37° C. for 60 min. and at 4° C. for 2 hours. This treatment solubilized 68.5% of the precipitated complexes. When the serum containing these solubilized complexes was subjected to ultracentrifugation in SDG, 31.1% of the antibody molecules were found in the 7S region (mean of two experiments); 10.8% of the antigen (BSA) was located in the 4-5S region, and less than 1% appeared in the 7S region (FIG. 6). The remaining portions of antigen and antibody were distributed in the heavier fractions of the gradient. Consequently, upon solubilization by C a large portion of complexed antibody molecules are freed of antigen.

In subsequent experiments, fractions corresponding to the 7S peak were pooled and portions submitted to treatment with goat anti-C3, anti-transferrin or normal goat serum. The results clearly demonstrated that the antibody was selectively precipitated only by anti-C3 serum (41%), not by the controls, anti-transferrin (2.8%), normal goat serum (3%) or by anti-BSA (7%). These experiments further confirm that a considerable amount of the solubilized antibody was not bound to the antigen but carried C3 determinants.

DISCUSSION

Despite the many antigen nonspecific assays currently available to detect ICs or like materials in biologic fluids, criticism has been voiced for most (13), and the drawbacks of these assays are considerable (1). However, because ICs appear to be involved in the immunopathology of many diseases and exert profound effects on humoral and cellular immune responses (1,14), the development of new, more specific techniques for IC-detection is, in our opinion, justifiable. We have described here the use of F(ab')2 anti-C3 antibody in a solid phase radioimmunoassay for the detection and partial characterization of C-fixing ICs in human and animal sera. The reagents used in this highly sensitive anti-C3 assay are simple to prepare or commercially available. Results not shown demonstrated that the principle of enzyme immunoassay can be easily applied to preclude the use of radioisotopes as well as assay by binding to staphylococcal protein A. The assay, like all other non-antigen specific IC assays, does not distinguish between nonspecifically aggregated Ig and antigen-complexed Ig. However, we believe that most nonspecific aggregates are formed in vitro during blood clotting and serum preparation. Therefore, the addition of EDTA during blood collection would prevent C-fixation to such aggregates without affecting the detection of ICs formed in vivo and containing C in the anti-C3 assay. Moreover, the assay is not affected by non-IC substances such as polyanions, endotoxins, nucleic acid, RFs and anti-lymphocyte antibodies that are known to interfere with many of the existing IC detection techniques (1). Our use of F(ab')2 anti-C3, instead of whole IgG anti-C3 outlined in a soluble anti-C3 assay by others (15), eliminates false positivity due to the presence of RFs, unless the RFs represent part of C-fixing ICs. The additional advantage over the Clq assays is that the anti-C3 solid phase assay detects ICs that fix C activated not only via the classical pathway but also via the alternative pathway. It is known that IgM and IgG antibodies activate the classical C pathway (16,17) whereas those of the IgA and IgE class activate the alternative C pathway (18,19). Unlike the Clq deviation and Clq and cause false positive results, the use of anti-Ig antibody as the final reagent in our solid phase anti-C3 assay permits detection of Ig-containing substances only.

Although we have some data on the size of ICs detected by the anti-C3 assay (see below), the required ratio of antigen to antibody and amount of C fixation for an IC to become detectable are unknown. There is little agreement in the literature about the molecular composition or minimum size of IgG-type ICs that can activate C; some investigators advocate the doublet $Ab_2Ag_1$ (20), others claim no less than a tetramer of antibody (21), whereas still others have shown activation of the classical pathway of C by a single IgG molecule binding a monovalent hapten (22). In general, it would appear that fixation of C by a soluble ICs made with IgG antibodies requires a lattice structure containing more than two or three antibody molecules (23).

When we applied the anti-C3 assay to the detection of C-fixing ICs in sera, we found a high incidence of such ICs in patients with SLE, rheumatoid arthritis, Felty's, Reiter's and Sjögren's syndromes and acute glomerulonephritis and to a lesser degree in neoplasia. Previously, IC-like materials were detected in sera of SLE patients by a variety of procedures (24,25), and IC determination were often found useful in following the course of disease in patients with SLE (26,27). Although glomerular elution studies indicated a role for DNA-anti-DNA complexes in the pathogenesis of SLE nephritis (28), direct evidence of circulating DNA-anti-DNA complexes has been controversial (29,30). However, mice with spontaneous SLE-like syndromes clearly form a variety of complexes including DNA-anti-DNA, RF-Ig and retroviral gp70-anti-gp70 (31). According to many assays, ICs are present in persons with Felty's (32), Reiter's (33) and Sjögren's (34) syndromes, but again the nature of the materials detected has not yet been defined. ICs have also been found in patients with infectious endocarditis (35) and the value of IC-determinations in the prognosis and management of such patients is clear (35,36). C-fixing ICs or like materials have also been observed in the course of leukemia (37) and a variety of other malignancies; in fact a role has been proposed for such complexes in tumor immunity, and IC measurement may have substantial prognostic value in such patients (reviewed in 1, 38). In malignancies the nature of complexes detected often remains undefined, despite some evidence that such patients sometimes have specific tumor antigen-antibody complexes in their sera and kidney deposits (reviewed in 1, 38). We (39) and others (40–42) are using a variety of physicochemical and immunochemical procedures as well as absorption to substances that bind ICs to characterize antigens in the ICs detected by the various techniques. Anti-C3 bound to insoluble matrices should be helpful in such attempts.

Sera in which ICs or like materials have been detected are being evaluated in several laboratories to determine the size of the reactive materials. In most of these studies the materials that react with substrates which detect ICs have been found to be mainly heavy (>19S) or intermediate (8–19S) in size in agreement with the concept that complexes are composed of multiple antigen-antibody molecules and sometimes C components. However, low molecular weight (7–8S) materials, reactive with C1q and Raji cells have also been detected in some sera of patients with SLE (25,43), Lyme arthritis (44), IgA deficiency (45) and other disorders. In using SDG ultracentrifugation to analyze materials reactive in the anti-C3 assay, we found heavy and/or intermediate size complexes in some sera. However, in sera from several patients the F(ab')2 anti-C3 reactivity was primarily, if not exclusively, confined to the 7–8S fractions. Not only F(ab')2 anti-C3 but also conglutinin bound the 7–8S fractions, and binding was specific since it was inhibited by anti-C3 or conglutinin in the fluid phase. Particularly patients with more generalized disease were those with intermediate and heavy complexes in their sera, whereas patients with less severe disease had predominantly the 7–8S component. This 7–8S material, which contained IgG that bound to F(ab')2 anti-C3 and conglutinin, may well represent the antibody moiety of ICs along with some small C3 fragments generated after C-induced IC solubilization. Solubilization of immune precipitates mediated by C in fresh serum has been described by Miller and Nussenzweig (10). The alternative C pathway mediates the solubilization, since factor B, factor D, properdin, C3 and $Mg^{++}$ must be present, and the apparent sequence is insertion of C3b into the immune precipitates to form properdin and factor B dependent convertase (46). The classical C pathway alone is incapable of solubilizing ICs (47), possibly because the assembled classical C3 convertase (C42), in contrast to the properdin- and factor B-dependent C3 convertase (C3b,P,B), has very short half-life (48,49) and therefore binds too few C3b molecules to disrupt the antigen-antibody lattice. Nevertheless, activation of the classical C pathway greatly enhances the solubilizing activity of the alternative pathway (47). Solubilization does not seem to result from rupture of all the antigen-antibody bonds considering that almost all the antigen remains ammonium sulfate-precipitable (10) and is, therefore, complexed after solubilization. In the present experiments, double labeling of antigen and antibody left little doubt that most of the antigen actually remained complexed; however, many antibody molecules (~30%) were freed during the C-induced solubilization process. The presence of free antibody molecules is possible due to the fact that certain antigens, as that used here, at equivalence bind several antibody molecules. Whether solubilization of ICs and generation of free antibody molecules takes place in vivo remains to be demonstrated, but our results suggest that is the case. On the antibody molecules, bound C3 may be degraded by serum enzymes such as B1H and C3b inactivator (reviewed in 1) leaving attached small fragments (i.e. C3d) that are the light-weight molecules we found reactive with anti-C3 and conglutinin. We are currently analyzing these low molecular weight reactants for binding substances like C1q, RF and cell receptors and subsequent biologic activity, if any. Conceivably, their light weight may preclude deposition in tissues and so "IC disease" is circumvented. Interestingly enough, Miller et al (50) observed that IC solubilized from mouse lymphocytes by C lost their ability to bind to fresh lymphocytes. These authors also observed that in older NZBxW mice with advanced disease there was a reduced C-mediated IC solubilization (51). Others (52) suggested that the alternative C pathway may be important in resolving ICs deposited in the kidney during experimental acute serum nephritis. Our indirect findings suggest that patients with generalized processes may become deficient in C-induced solubilization of ICs. The cause could be rapid consumption of C resulting from a high rate of IC formation, inability to assemble the C3b,P,B convertase or high affinity of the antigen-antibody bonds.

Industrial Application

The inventive concept which has been described has application in immunological diagnostics and treatment of various disorders and diseases resulting from or associated with the presence of immune complexes.

While the invention can be carried out in many ways, the examples given in the preceding discussion are presently the best mode of carrying out the invention. The foregoing must not be considered as limiting in any way, except as to the principle of the assay.

Figure 7:
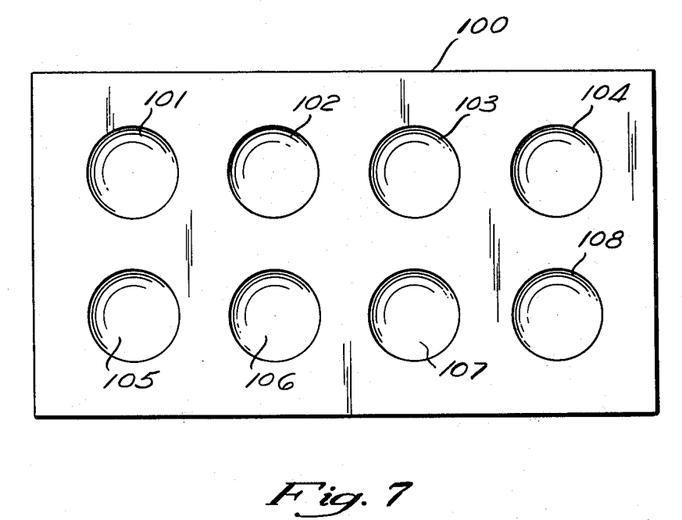
FIG. 7 is microtiter plate prepared according to this invention.

It is convenient to prepare, either for future use in the same laboratory or for sale and distribution to laboratories, hospitals, pre-coated substrates for use in carrying out the assay. A very simplified substrate is shown, merely as exemplary, in FIGS. 7 and 8. The substrate 100 comprises a sheet of suitable material with one or more areas which are suitable for being coated with a reagent specific for C3. Eight such areas, in this instance, U-shaped wells, are indicated at 101 through 108. It is to be clearly understood, however, that no criticality is attached either to the size or shape of the substrate or the areas, a flat substrate with U-shaped wells being merely a simple and expedient shape which is readily available. The substrate may, of course, comprise as many areas to be coated as may be desired.

Figure 8:
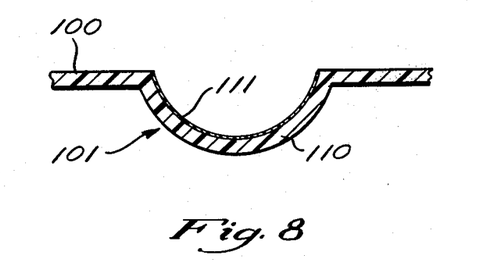
FIG. 8 is an enlarged cross-section of one well of the plate of FIG. 7 showing the active layer in greatly magnified thickness.

FIG. 8 depicts, for illustrative purposes only, one area which has been prepared for use in the C3 assay of this invention. Well 101, for example, is coated, as described hereinbefore or in any other convenient manner, with F(ab')2 anti-C3 in a layer illustratively indicated at 111. It will be immediately apparent that the thickness of the substrate 110 is infinitely thicker than the F(ab')2 anti-C3 layer, rather in the dimension or ratio in the figure. In the exemplary embodiment, the substrate is a polystyrene flexible microtiter plate of the type which is conventionally used in agglutination and comparable tests and which is readily available on the market. The size, shape and composition of the substrate is, however, absolutely immaterial so long as no adverse reaction occurs and the substrate is in a configuration which is suitable for use in RIA (radioimmunoassay) or ELISA, or other, detection or measuring techniques.

It is within the intent and scope of this invention to provide, either for in-laboratory use or for sale to others, an assay kit which, conveniently will include a substrate having at least one measurable area coated with F(ab')2 anti-C3. (By measurable area, we mean an area which can be subjected to measurement or detection by RIA, ELISA or other counting, observation or measuring technique.) In addition, the kit may include radio- or enzyme- linked IgG anti-human IgG, or generally equivalent, detectable reagent. (By detectable reagent, we mean a reagent which will couple with F(ab')2 anti-C3 and which can be detected qualitatively at least and preferably quantitatively. RIA and ELISA reagents are typical of such detectable reagents.) A preferred detectable reagent for the kit embodiment of this invention is radiolabeled staphyloccal protein A, which is available in stable, consistent quality form and which is easily detected as a means of measuring, by RIA methods, the quantity of C3-IgG bound to the coated substate. The kit may also include other reagents, if desired, to facilitate the carrying out of the assay of this invention.

The invention resides in the discovery and in the selection of the coating for the substrate, the resulting substrate, and the overall assay, and not in particular reagents, material, or conditions and the claims which are appended hereto are to be so understood. REFERENCES 1. Theofilopoulos, A. N. and F. J. Dixon. 1979. The biology and detection of immune complexes. Adv. Immunol. 28, 89–220.
2. Nisonoff, A., F. C. Wissler, L. N. Lipman and D. L. Woernley. 1960. Separation of univalent fragments from the bivalent rabbit antibody molecule by reduction of disulfide bonds. Arch. Biochem. Biophys. 89:230–244.
3. McConahey, P. J. and F. J. Dixon. 1966. A method of trace iodination of proteins for immunologic studies. Int. Arch. Allery 29:185–189.
4. Andrews, B. S., R. A. Eisenberg, A. N. Theofilopoulos, S. Izui, C. B. Wilson, P. J. McConahey, E. D. Murphy, J. B. Roths and F. J. Dixon. 1978. Spontaneous murine lupus-like syndromes. Clinical and immunopathological manifestations in several strains. J. Exp. Med. 148:1198–1215.
5. Wilson, C. B. and F. J. Dixon. 1971. Quantitation of acute and chronic serum sickness in the rabbit. J. Exp. Med. 134:7S–18S.
6. Mancini, G., A. O. Carbonara and J. F. Heremans. 1965. Immunochemical quantitation of antigens by single radial immunodiffusion. Immunochem. 2:235–254.
7. Theofilopoulos, A. N., C. B. Wilson and F. J. Dixon. 1976. The Raji cell radioimmune assay for detecting immune complexes in human sera. J. Clin. Invest 57:169–182.
8. Eisenberg, R. A., A. N. Theofilopoulos and F. J. Dixon. 1977. Use of bovine conglutinin for the assay of immune complexes. J. Immunol. 118:1428–1434.
9. Singer, J. M. and C. M. Plotz. 1956. The latex fixation test. I. Application to the serologic diagnosis of rheumatoid arthritis. Amer. J. Med. 21:888–892.
10. Miller, G. W. and V. Nussenzweiz. 1975. A new complement function: solubilization of antigen-antibody aggregates. Proc. Natl. Acad. Sci. USA 72:418–422.
11. Lachman, P. J. 1967. Conglutinin and immunoconglutinins. Adv. Immunol. 6:479–527.
12. Creighton, W. D., P. H. Lambert and P. A. Miescher. 1973. Detection of antibodies and soluble antigen-antibody complexes by precipitation with polyethylene glycol. J. Immunol. 111:1219–1227.
13. Schur, P. H. 1978. Immune complex assays: the state of the art. N. Eng. J. Med. 298:161–162.
14. Haakenstad, A. O. and M. Mannik. The biology of immune complex. In: Autoimmunity. Talal, N. (ed.). Academic Press, New York, p. 278.
15. Jacobs, R. and M. Reichlin. 1979. A new quantitative assay for immune complexes. Fed. Proc. 38:1359. (Abs.).
16. Müller-Eberhard, H. J. 1975. Complement. Ann. Rev. Biochem. 44:697–724.
17. Spiegelberg, H. L. 1974. Biological activities of immunoglobulins of different classes and subclasses. Adv. Immunol. 19:259–294.
18. Ishizaka, T., C. M. Sian and K. Ishizaka. 1972. Complement fixation by aggregated IgE through alternate pathway. J. Immunol. 108:848–851.
19. Spiegelberg, H. L. and O. Götze. 1972. Conversion of C3 proactivator and activation of the alternative pathway of complement activation by different classes and subclasses of human immunoglobulins.Fed. Proc. 31:655 (Abs.).
20. Cohen, S. 1968. The requirement for the association of two adjacent rabbit γG-antibody molecules in the fixation of complement by immune complexes. J. Immunol. 100:409–413.
21. Hyslop, N. E., R. R. Dourmashkin, N. M. Green and R. R. Porter. 1970. The fixation of complement and the activated first component (C1) of complement by complexes formed between antibody and divalent hapten. J. Exp. Med. 131:783–802.
22. Goers, J. W., R. J. Ziccardi, V. N. Schumaker and M. M. Glovsky. 1977. The mechanism of activation of the first component of complement by a univalent hapten-IgG antibody complex. J. Immunol. 118:2182–2191.
23. Mannik, M., W. P. Arend, A. P. Hall and B. C. Gilliland. 1971. Studies on antigen-antibody complexes. I. Elimination of soluble complexes from rabbit circulation. J. Exp. Med. 133:713–739.
24. Zubler, R. H., G. Lange, P. H. Lambert and P. A. Miescher. 1976. Detection of immune complexes in unheated sera by a modified $^{125}$I-C1q binding test. Effect of heating on the binding of C1q by immune complexes and application of the test to systemic lupus erythematosus. J. Immunol. 116:232–235.

25. Gabriel Jr., A. and V. Agnello. 1977. Detection of immune complexes. The use of radioimmunoassays with C1q and monoclonal rheumatoid factor. J. Clin. Invest. 59:990–1001.

26. Levinsky, R. J., J. S. Cameron and J. F. Soothill. 1977. Serum immune complexes and disease activity in lupus nephritis. Lancet 1:564–567.

27. Pussell, B. A., C. M. Lockwood, D. M. Scott, A. J. Pinching and D. K. Peters. 1978. Value of immune-complex assays in diagnosis and management. Lancet 2:359–363.

28. Koffler, D., V. Agnello and H. G. Kunkel. 1974. Polynucleotide immune complex in serum and glomeruli of patients with systemic lupus erythematosus. Amer. J. Pathol. 74:109–124.

29. Izui, S., P. H. Lambert and P. A. Miescher. 1977. Failure to detect circulating DNA-anti-DNA complexes by four radioimmunological methods in patients with systemic lupus erythematosus. Clin. Exp. Immunol. 30:384–392.

30. Bruneau, C. and J. Benveniste. 1979. Circulating DNA-anti-DNA complexes in systemic lupus erythematosus. Detection and characterization by ultracentrifugation. J. Clin. Invest. 64:191–198.

31. Theofilopoulos, A. N., P. J. McConahey, S. Izui, R. A. Eisenberg, A. B. Pereira and W. D. Creighton. 1980. A comparative immunologic analysis of several murine strains with autoimmune manifestations. Clin. Immunol. Immunopath., in press.

32. Andreis, M., E. R. Hurd, J. LoSpalluto and M. Ziff. 1978. Comparison of the presence of immune complexes in Felty's syndrome and rheumatoid arthritis. Arthritis Rheum. 21:310–315.

33. Rosenbaum, J. T., A. N. Theofilopoulos, H. O. McDevitt, A. B. Pereira, D. Carson and A. Calin. 1980. Presence of circulating immune complexes in Reiter's syndrome and ankylosing spondylitis. Lancet, submitted.

34. Lawley, T. J., H. M. Moutsopoulos, S. I. Katz, A. N. Theofilopoulos, T. M. Chused and M. M. Frank. 1979. Demonstration of circulating immune complexes in Sjögren's syndrome. J. Immunol. 123:1382–1387.

35. Bayer, A. S., A. N. Theofilopoulos, R. A. Eisenberg, F. J. Dixon and L. B. Guze. 1976. Circulating immune complexes in infective endocarditis. N. Engl. J. Med. 295:1500–1505.

36. Bayer, A. S., A. N. Theofilopoulos, F. J. Dixon and L. B. Guze. 1979. Use of circulating immune complex levels in the sero-differentiation of endocarditic and non-endocarditic septicemias. Amer. J. Med. 66:58–62.

37. Carpentier, N. A., G. T. Lange, D. M. Fiere, G. J. Fournie, P. H. Lambert and P. A. Miescher. 1977. Clinical relevance of circulating immune complexes in human leukemia. J. Clin. Invest. 60:874–884.

38. Theofilopoulos, A. N. and F. J. Dixon. 1979. Immune complexes associated with neoplasia. In: Immunodiagnosis of Cancer. Herberman, R. (ed.). M. Dekker, Inc., New York.

39. Theofilopoulos, A. N., R. A. Eisenberg and F. J. Dixon. 1978. Isolation of circulating immune complexes using Raji cells. J. Clin. Invest. 61:1570–1581.

40. Chenais. F., G. Virella, C. C. Patrick and H. H. Fudenberg. 1977. Isolation of soluble immune complexes by affinity chromatography using staphylococcal protein A-sepharose as substrate. J. Immunol. Meth. 18:183–192.

41. Casali, P. and P. H. Lambert. 1979. Purification of soluble immune complexes from serum using polymethylmetacrylate beads coated with conglutinin or C1q. Clin. Exp. Immunol. 37:295–309.

42. Natali, P. G., L. Walker and M. A. Pellegrino. 1980. Isolation of soluble immune complexes from serum using protein A-bearing Staphylococcus aureus bacteria: Separation of the antigen from immune complex and production of antisera. Clin. Immunol. and Immunopath. 15:76–87.

43. Robinson, M. F., J. L. Roberts, J. Verrier Jones and E. J. Lewis. 1979. Circulating immune complex in patients with lupus and membranous glomerulonephritis. Clin. Immunol. Immunopathol. 14:348–360.

44. Hardin, J. A., L. C. Walker, A. C. Steere, T. C. Trumble, K. S. K. Tung, R. C. Williams, Jr., S. Ruddy and S. E. Malawista. 1979. Circulating immune complexes in Lyme arthritis. J. Clin. Invest. 63:468–477.

45. Kwitko, A. O., P. E. McKenzie, D. J. C. Shearman, A. A. Gormly and A. J. Woodroffe. 1979. Circulating immune complexes in IgA deficiency. Clin. Exp. Immunol. 38:45–51.

46. Takahashi, M., B. F. Tack and V. Nussenzweig. 1977. Requirements for the solubilization of immune aggregates by complement. Assembly of a factor B-dependent C3-convertase on the immune complexes. J. Exp. Med. 145:86–100.

47. Takahashi, M., S. Takahashi, V. Brade and V. Nussenzweig. 1978. Requirements for the solubilization of immune aggregates by complement. The role of the classical pathway. J. Clin. Invest. 62:349–358.

48. Fearon, D. T. and K. F. Austen. 1975. Properdin: binding to C3b and stabilization of the C3b-dependent C3 convertase. J. Exp. Med. 142:856–863.

49. Schreiber, R. D., R. G. Medicus, O. Götze and H. J. Müller-Eberhard. 1975. Properdin and nephritic factor-dependent C3 convertases: requirement of native C3 for enzyme formation and the function of bound C3b as properdin receptor. J. Exp. Med. 142:760–772.

50. Miller, G. W., P. H. Saluk and V. Nussenzweig. 1973. Complement-dependent release of immune complexes from the lymphocyte membrane, J. Exp. Med. 138:495–507.

51. Miller, G. W., A. D. Steinberg, I. Green and V. Nussenzweig. 1975. Complement-dependent alterations in the handling of immune complexes by NZB/W mice. J. Immunol. 114:1166–1170.

52. Bartolotti, S. R. and D. K. Peters. 1978. Delayed removal of renal bound antigen in decomplemented rabbits with acute serum sickness. Clin. Exp. Immunol. 32:199–206.

53. Wilson, M. B. and P. K. Nakane: (1978). Recent developments in the periodate method of conjugating horseradish peroxidase (HRPO) to antibodies in immunofluorescence and related staining techniques. Edited by W. Knapp, K. Hombar and G. Wick, Elsevier/North Holland Biomedical Press, pg. 215.

54. Theofilopoulos, A. N., C. B. Wilson and F. J. Dixon (1976). The Raji cell radioimmune assay for detecting immune complexes in human sera. J. Clin. Invest. 57:169.

55. Jacobs, R. and Reichlin, M. The new Quantitative Assay for Immune Complexes to be presented at the Federation of American Societies for Experimental Biology, Mar. 1, 1980, Abstract, Volume 38, p. 1359, No. 5977.

What is claimed is:

1. An assay method for immune complexes comprising the steps of binding F(ab')2 anti-C3 to a solid substrate, reacting the fluid suspected of containing immune complexes with the bound F(ab')2 anti-C3, and determining the amount of bound immune complexes on said substrate.

2. In the assay for immune complexes wherein the immune complexes are bound with a binding reagent having excess binding sites and the quantity of bound immune complexes is determined by detecting the quantity of sites not bound by immune complexes, the improvement wherein the binding reagent is F(ab')2 anti-C3 bound to a solid matrix.

3. In the assay for immune complexes wherein binding means are provided for binding such immune complexes, reacting said binding means with said immune complexes, reacting sites on said binding means which are not bound to immune complexes with a detectable reagent means and quantitatively measuring the amount of detectable reagent means, the improvement comprising a solid substrate and F(ab')2 anti-C3 reagent bound on the surface of said substrate as the binding means.

4. An assay means for use in connection with samples suspected of containing immune complexes and reagents capable of being quantitatively measured when bound to such assay means, said assay means comprising a solid substrate and a layer of F(ab')2 anti-C3 reagent bound on the surface of said solid substrate.

5. A method for determining immune complexes comprising reacting said immune complexes with binding means comprising a solid substrate coated with F(ab')2 anti-C3 and quantitatively determining the amount of immune complexes bound on said substrate coated with F(ab')2 anti-C3.

* * * * *

UNITED STATES PATENT AND TRADEMARK OFFICE
CERTIFICATE OF CORRECTION

PATENT NO. : 4,342,566

DATED : August 3, 1982

INVENTOR(S) : Theofilopoulos, et al.

It is certified that error appears in the above-indentified patent and that said Letters Patent is hereby corrected as shown below:

Column 1, line 4, please insert the following:

This invention was made with government support under Grant Number CA 23322 awarded by The National Institutes of Health. The government has certain rights in this invention.

Signed and Sealed this

Twenty-ninth Day of March, 1994

Attest:

BRUCE LEHMAN

*Attesting Officer*   Commissioner of Patents and Trademarks